United States Patent [19]

Dee et al.

[11] Patent Number: 4,672,964
[45] Date of Patent: Jun. 16, 1987

[54] SCALPEL WITH UNIVERSALLY ADJUSTABLE BLADE

[76] Inventors: Robert N. Dee, 31 Tuckahoe Ave., Eastchester, N.Y. 10709; Charles Reich, 57 W. 57th St., New York, N.Y. 10019

[21] Appl. No.: 831,801

[22] Filed: Feb. 21, 1986

[51] Int. Cl.⁴ ............................................. A61B 17/32
[52] U.S. Cl. ...................................... 128/305; 30/321
[58] Field of Search .............. 128/305, 304, 346, 340; 30/329, 339, 321, 286, 285, 295, 87

[56] References Cited

U.S. PATENT DOCUMENTS 2,316,985  4/1943  Niedermayer ..................... 30/339 X
3,609,864 10/1971  Bassett .............................. 30/339 X
3,922,784 12/1975  Prince et al. .......................... 30/317
3,981,308  9/1976  Schlein ............................... 128/346

FOREIGN PATENT DOCUMENTS 151270 10/1984  Mexico ............................... 128/305
490072  6/1970  Switzerland .................... 128/303 R Primary Examiner—Michael H. Thaler
Attorney, Agent, or Firm—Jerome Bauer

[57] ABSTRACT

A single scalpel having a universally adjustable blade mounted to the scalpel handle for selected positioning through an arc of at least 90° with respect to the axis of the handle and through an arc of at least 360° about the axis of the handle thereby enabling the single scalpel to be used at any required angle and position without changing blades or scalpels.

9 Claims, 5 Drawing Figures

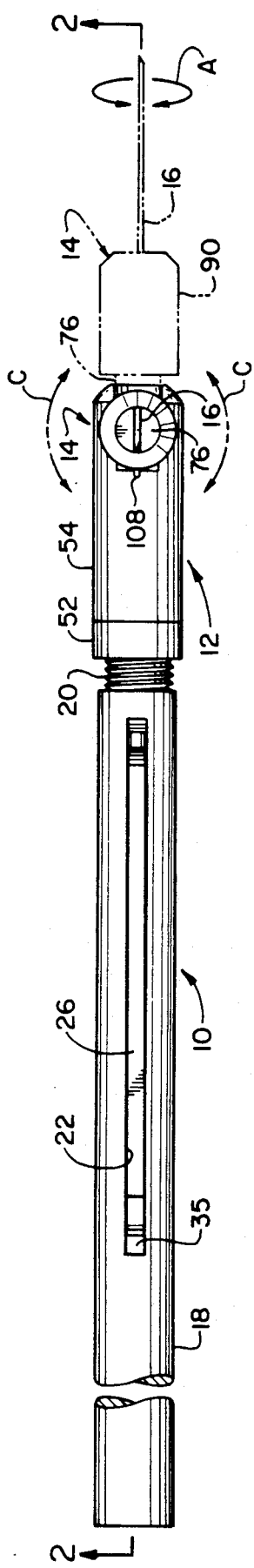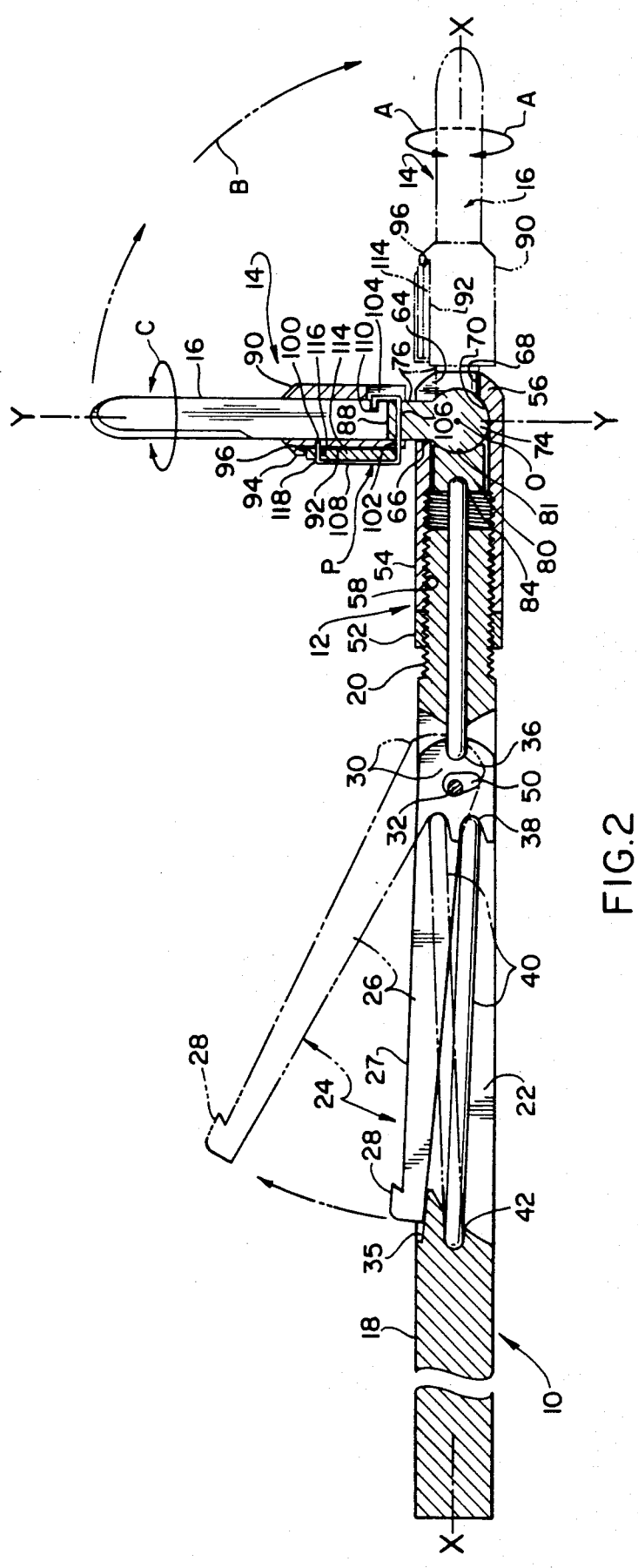
FIG.1
FIG.2

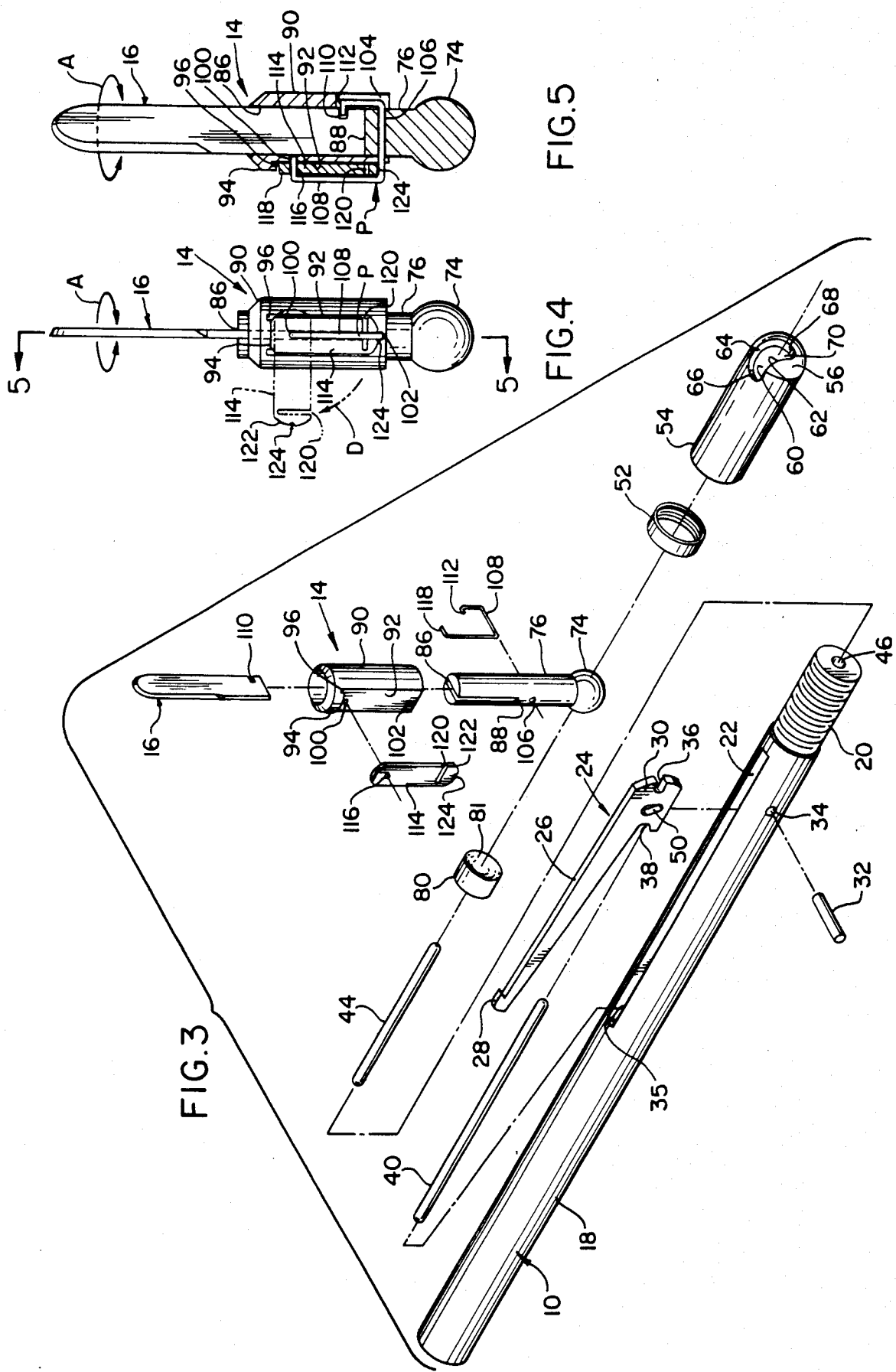

SCALPEL WITH UNIVERSALLY ADJUSTABLE BLADE

BACKGROUND OF THE INVENTION

The present invention relates to a surgical scalpel and in particular to a periodontal scalpel, although not specifically limited thereto, wherein the blade is universally adjustable.

Scalpels presently used for general and dental surgery, particularly periodontal surgery are very small in size and of the type generally fixed in construction in that the cutting blade, when mounted in the chucked end of the scalpel, is fixed in position. Hence, although the cutting blade may be removed from the chuck to be replaced by blades of different shapes and sizes to enable the periodontist to manipulate the blade into smaller confined spaces, once the blade is chucked to the handle it is not movable with respect to the handle. As a consequence, during the performance of surgery, it is necessary for the surgeon to have a large number of handles already mounted with cutting blades each of different sizes, shapes and angular positions so that he may draw upon and select any one of those that he needs at any given time.

Since this is a severe drawback and limitation upon the maneuverability of the surgeon, it is helpful to have a single scalpel that he may manipulate in a single hand and which may have the capability of permitting the blade to be pivoted at any universal angle so desired at the moment required by the surgeon and locked in the angle of positioning and to permit the blade to be removed and substituted for by another blade.

Attempts have been made to provide scalpels with adjustably positionable blades. For example, reference can be made to U.S. Pat. Nos. 3,609,864 and 4,275,735. In the latter U.S. Pat. No. 4,275,735, a hollow handle is provided, having at its distal end a plurality of slots into a selected one of which a given blade is placed. Within the handle is mounted a retractable shank, at the anterior end of which is a ring which overlies the blade and which is adapted to secure the blade in a given slot. This device does not provide for the ability of the blade to be adjusted or enable its adjustment after insertion in the slot, nor does it provide the surgeon with the degree of maneuverability and adaptability as is desirable at any given moment during the operative procedure.

In the earlier patent, U.S. Pat. No. 3,609,864 a scalpel is shown in which the blade is held on a plate-like blade holder which is provided with a spherical anchoring end held within a socket formed in the distal end of a handle and held therein by an internal clamping rod. The socket is provided with a narrow slot through which the plate holder passes and in which it is movable in the single plane of the plate. The blade thus has limited movement at the anterior end of the handle in a single plane. Rotation of the blade about the longitudinal axis of the blade is not possible, nor is universal positioning of the blade holder.

It is an object of the present invention to provide a scalpel which enables universal positioning of the cutting edge of the blade relative to the axis of the handle, in situ, i.e., while the blade is mounted on the handle and at any desired moment during the surgery.

It is an object of the present invention to provide a scalpel in which the blade is easily and simply mounted at the end of a handle so as to be universally adjustable in situ and still have all of the strength and rigidity necessary to sucessfully carry out surgery.

It is, of course, an object of the present invention to provide a scalpel which is easily disassembled for sterilization and thereafter reassembled, which can employ conventional disposable and/or reusable blades.

It is a specific object of the present invention to provide a scalpel having a novel chuck mechanism for universally positioning the blade, it being a more specific object to provide the chuck mechanism so that it is operable by simple manipulation of the handle by the user during actual use of the scalpel.

These objects as well as others will be apparent from the following disclosure.

SUMMARY OF THE INVENTION

According to the present invention, a scalpel is provided having an elongated handle conveniently shaped in the form of a shaft, although not limited thereto, a blade located in a blade holder mounted at the distal end of the shaft, as to be universally adjustable, whereby the blade is orientated in any one of a plurality of selected directions relative to the axis of the handle, namely, by relatively rotating the handle and blade about the axis of the shaft and/or swinging the blade in an arc subtended by the axis of the shaft and in a line perpendicular thereto, and correspondingly rotating the holder about its own axis.

In particular, the blade is mounted or held in a chuck having a ball-shaped base, which is set into a spherical socket formed in a cylindrical chuck housing, co-axially mounted at the end of the shaft. The end of chuck housing is cut in the form of a cleft defined by the axis of the shaft-handle and a perpendicular line thereto. Mounted within the chuck housing is an operable stop member adapted to engage the ball and fixedly hold the chuck in its selected position. The stop member is operated by a crank mechanism located in the shaft-handle, which is operable and easily manipulated by the operating hand of and during surgery by the surgeon via a lever extending along the surface of the shaft actuating an eccentric crank to cause the stop member to move axially within the housing into and out of engagement with the ball base of the chuck.

In another aspect of the invention, the chuck is provided with an axial slot in which the blade is received, and a sleeve surrounding the blade and slot retains the blade therein. The sleeve is secured to the chuck by a spring member passing through the sleeve and the chuck. Preferably, the spring also engages the blade preventing axial movement of the blade in the chuck, the spring being manually depressible, to release the blade for removal from the chuck. A removable plate is provided for biasing the spring against depression.

Full details of the present invention are set forth in the following description and illustrated in the accompanying drawings.

BRIEF DESCRIPTION OF THE DRAWINGS

In the Drawings:

FIG. 1 is a top plan view of the scalpel of the present invention;

FIG. 2 is a cross-section taken along the diametrical plane 2—2 of FIG. 2;

FIG. 3 is an exploded isometric view of the scalpel of the present invention;

FIG. 4 is a plan view of the chuck employed in the scalpel of the present invention as viewed from the left-hand end of FIG. 2 and shown separate and apart from the scalpel; and FIG. 5 is a sectional view of the chuck taken along the plane 5—5 of FIG. 4.

DESCRIPTION OF THE INVENTION

As seen in FIGS. 1 and 2, the scalpel of the present invention comprises a handle generally identified 10, at the distal end of which is threaded a chuck housing generally identified 12, in which a chuck generally identified 14 is adjustably held to the chuck housing and in which a blade 16 is removably held. To understand the following description more readily, it should be understood that the handle 10, and chuck housing 12 may have any cross-section but are here shown as being cylindrical and have a common central longitudinal extent or axis, about which the scalpel blade 16 is rotatable, by manual manipulation, as shown by the arrow A in FIGS. 1, 2, 4, and 5. The chuck 14 is arranged within the chuck housing 12 to pivot within the range of a right angle or 90° as denoted by the double arrows B in FIG. 2, while the chuck 14 and blade 16 can rotate as a unit clockwise and counter-clockwise about the axis Y—Y of the blade in the directions denoted by the double arrows C in FIG. 2.

As seen in FIGS. 2 and 3, the handle 10 preferably comprises a solid shaft 18 made of surgical steel that may be knurled or sculptured (not shown) on its exterior surface as may be desired to facilitate its easy grasping by the surgeon or dentist. The outer surface at the forward or distal end of the shaft-handle is threaded as at 20 to provide a removable seat for the chuck housing 12. A longitudinally elongated through slot 22 is provided in the shaft 18 spaced therefrom toward the rear of the threaded distal end. The slot 22, has parallel sides which pass diametrically through the shaft 18 and has inserted therein a plate-like locking crank, generally denoted by the numeral 24.

The locking crank 24 comprises a lever arm 26 extending proximally, terminating in a raised finger ridge 28 for easy manipulation and has a depending eccentric crank head 30 at its distal end. The locking crank 24 is held within the slot 22 by a retaining pin 32 inserted through a bore 34 (FIG. 3) extending diametrically through the shaft 18 perpendicular to the plane of the sidewalls of the slot 22. A shallow groove 35 is cut in the shaft 18, at the rear of the slot 22, so that the finger ridge 28 at the proximal end of lever 26 seats therein. The groove 35 provides a rest stop which maintains the outer exposed surface 27 of the lever 26 in a generally parallel position to the axis of shaft 18 and positions the finger ridge 28 above the surface and out of the slot of the shaft 18. This is referred to hereinafter as the locking position.

Shallow recesses 36 and 38 are formed in both the forward and rear edges of the crank head 30, respectively. The rear recess 38, is arranged slightly below the forward recess 36 and receives therein the forward end of a locking rod 40 which extends along the rear of and through the slot 22, normally at a small downward incline to the central axis X—X of the shaft-handle 18, and which terminates in a blind seating bore 42 (FIG. 2) formed in the shaft 18. The recess 36, on the other hand, is located along the axis X—X and receives and retains the rear end of a second locking rod 44 which slidably passes through an axial through-bore 46 in the distal portion of the shaft 18.

The rear locking rod 40 is dimensioned so that with the lever 26 in the locking position, it continually braces and presses squarely between the end of the blind bore 42 and the recess 38 providing a force in the forward or distal direction on the crank head 30. This creates a counter-clockwise torque (as viewed in FIG. 2) on the crank head 30 which biases the lever 26 counter-clockwise causing the proximal end of the lever 26 to seat in the groove 35. Simultaneously, the forward locking rod 44 is extended in its distal most or forward direction, by the force of the crank head 30.

It is to be noted that the function of the retaining pin 32 is to insure that the crank 24 does not fall out of the slot 22, should any one of the rods 40 or 44 become dislodged for any reason; otherwise, it does not function as a pivot pin, pivot axis, or cam surface. To this end, the retaining pin 32 passes through an enlarged hole 50 formed in the crank head 30 to permit the crank head 30 to move without restriction by the pin. In operation, the crank head 24 merely shifts, revolves or otherwise moves eccentrically about the pin 32 without necessarily touching it.

The crank lever 26 is manually swingable upwardly from its seat in a clockwise direction about the pin 32, against the bias imparted to it by the locking rod 40. As the rear end 28 of the crank lever 26 is lifted clockwise, the rear locking rod 40 will lift upwardly at its forward end allowing the head 30 to move rearward relative to the pin 32 because of the enlarged size of the hole 50. This leaves room for the rod 44 to slide rearward within the bore 46 because it is relieved from the pressure and bracing force applied by the rear locking rod 40 on the crank head 30 and consequently relieves the forward tensioning force on the forward locking rod 44. This position of the rod 40 is shown in the dot-dash lines of FIG. 2 and is referred to hereinafter as the release position.

The locking rods 40 and 44 are preferably stainless steel, spring grade, round or bar stock. Such material has sufficient flexibility to allow resilient distortion, i.e., bowing as well as low friction slidability. The shape or flare of the recesses 36 and 38 as well as of the bore 42 are not critical, but should be sufficient to permit movement of the locking rods 40 and 44 when necessary and turning or rotation of the head 30 for the function described.

When the rod 40 and head 30 are in their solid line locking positions, the lever 26 is held in the slot 22 against the seat 35. The forward locking rod 44 is thereby pressed forward at its recess 36 to its locking position to extend and slide in its guide bore 46 to aid in locking the blade 16 in its adjusted position.

Turning now to FIGS. 2 and 3, the chuck housing 12 for rotatably mounting the blade 16 to the handle is held in its desired position on the distal end of the shank 18 by a jamb nut 52 and comprises an extended hollow sleeve 54 substantially closed at its forward end by a partial enclosing spherical wall 56. The sleeve 54 is provided with an internally threaded rear end 58 adapted to screw over the forward threaded end 20 of the shaft-handle 18 to any desired angle of at least 360° about an axis extending through the length of the handle 10 and to be locked in such position of adjustment by the lock or jamb nut 52. Both the shaft-handle 18 and the inner surface of the sleeve 54 of the chuck housing 12 may be provided with appropriate shoulders or retaining washers (not shown) against which rotation of the sleeve 54 is limited and locked and which enables the sleeve 54 to be held in fixed place during use by the surgeon, in lieu of using the jamb or lock nut 52.

A cleft or cut-away opening 60 is formed at the distal end of the chuck housing sleeve 54 by removing a sector of the enclosing spherical wall 56. The cleft 60 is defined by the axially or longitudinally extending parallel walls 62 and 64 and semi-round transverse rear and forward walls 66 and 68, respectively. In this manner, the defines of the cleft 60 provide, in cross-section (FIG. 2), a substantially rectangular opening in the housing sleeve 54. The interior surface of the housing sleeve 54 as well as the adjacent partial sections of the cylindrical wall of the sleeve 54 are concavely formed to provide a spherical cup 70 into which the base 74 of the chuck 14 seats as seen in FIG. 2.

The chuck 14 as seen in detail in FIGS. 4 and 5 comprises the spherical base 74 and an extending cylindrical shank 76. In assembly, as seen in FIG. 2, the base 74 fits slidably within the cup 70 and the cylindrical shank 76 extends outwardly through the cleft 60. The cup 70, and the base 74 are dimensioned to have the same center "O" which passes through the axis "X" of the shaft 18 so that the ball 74 and cup 70 provide a smooth working joint that has universal movement within the cup 70. Similarly, the diameter of the chuck shank 76 and the distance between the parallel walls 62 and 64 are also dimensioned to allow free movement of the shank 76 between the relatively spaced end walls 66 and 68 that also includes rotative movement relative to the parallel walls 62 and 64.

In this configuration, the chuck shank 76 can be made to simultaneously swing through an arc of at least ninety (90°) degrees between the rear end wall 66 and the forward end wall 68 through the angle shown by the double arrow B, and rotate endlessly through an arc of at least 360° about the axis Y—Y as shown by double arrows C. The arc B can be increased or decreased by correspondingly changing the relative space between the limiting walls 66 and 68. Obviously, if the relative space is greater, the angle B will be greater.

To secure the chuck 14 in any one of its infinite positions, a locking plate 80 (FIG. 2) is located within the housing sleeve 54 in sliding abutment with the ball shaped base 74 of the chuck 14. The locking plate 80 has a spherical frontal engaging face 81 and is provided on its rear surface 82 with a blind bore 84 into which forward end of the front locking rod 44 is fixedly seated. When the forward locking rod 44 is moved forwardly (to the right as viewed in the drawing) by placing the crank 24 in the locking position as shown in solid lines in FIG. 2, the plate 80 is pushed and locked forward placing its front face 81 into secure abutment against the ball 74. This forces the ball 74 simultaneously against the spherical conforming cup surface 70 to chuck it thereto and thereby securely seats and locks the ball 74 against any further movement. Adjustment of the chuck 14 is made merely by lifting the raised finger ridge 28 of the lever 26 into the release broken-line position of FIG. 2 to displace the rod 40 to its broken-line release position thereby removing the tension on rod 44. This further releases the locking engagement of the locking plate 80 with the ball 74 permitting ball 74 to move universally relative to the chuck housing 12.

The surface of the ball-shaped base 74 of the chuck 14 and/or the spherical face 81 of the locking plate 80 can be conformingly shaped or provided with knurls, ratchet teeth or the like to insure and effect a more secure locking of the parts. The locking position is maintained during actual use of the scalpel, notwithstanding severe pressure placed thereon by the doctor, because the handle 10 of the scalpel is always contained within the encompassing hand of the doctor during use which prevents accidental pivoting or lifting of the lever arm 26 from its locked position. As long as the arm 26 is in its locked position, the rear and front locking rods 40 and 44 bias and lock the locking plate 80 in its locking position against the ball 74. Thus, while the lever arm 26 is encompassed within the surgeon's hand, it is not possible for the blade 16 to move from its adjusted position.

As seen in FIGS. 3 and 5, the blade 16 is removably accommodated in a cylindrical shaft 76 of the chuck 14 that is bifurcated at the end opposite the ball shaped base 74 to provide an open ended axial slot 86 having an inner wall 88. As seen in FIGS. 2, 3 and 5, the blade 16 is held in place in the slot 86 of the cylindrical shank 76 by a retaining ring 90 which is generally cylindrical on its inner surface and which has an internal diameter to fit closely about the shank 76. The ring 90 is provided with a chordal wall or land 92 on its outer surface and is left, when formed, with a covering shoulder 94 at the front edge of the land 92. The covering shoulder 94 overlaps a portion of the land 92 and forms a recess 96 therewith.

The retaining ring 90 is provided with a hole 100 in the chordal wall near the front end and a hole 102 near its rear end which passes through and in alignment along the longitudinal center line of the land 92. On the diametrically opposite side of the ring 90 from the rear hole 102 there is formed a slot 104 extending inwardly from the rear edge of the ring 90, for a short distance. The cylindrical shank 76 of the chuck 14 is provided with a diametrical through-bore 106 which extends just behind the inner wall 88 of the slot 86 into which the blade 16 is inserted.

A multi-angular spring 108 passes along and about the ring 90 extending through the bore 106 in the chuck shank 76 extending from the front hole 100 through the rear hole 102 into the lengthwise axial slot 104 of the ring 90. The blade 16, is itself formed with a notch 110 along its lower edge at point which opens to the slot 104 in the ring 90 so that the tail end 112 of the spring 108 will lodge and engage securely in the notch 110. The spring 108 is made of heavy gauge piano wire which is capable of being bent into shape on insertion into the ring 90, in situ, and yet retain its highly resilient nature after bending.

When positioned as shown in FIGS. 2, 4 and 5, the spring 108 locks the blade 16 in the chuck 14. Thereafter, the blade 16 may be released from the chuck 14 by applying depressing finger pressure against the rear end of the spring 108 at the point indicated by the numeral P in FIGS. 2, 4 and 5 so that the short tail end 112 of the spring 108 moves radially outward for the width of the slot 104 and fully out of the notch 110 in the blade 16. This frees the spring end 112 from engagement with the blade 16 for removal through the front end of the slot 86 and from the retaining ring 90. The blade 16 can also be easily replaced by inserting a similar blade through the ring 90 into the slot 86 of the chuck slot 88 after depressing the retaining spring 108 to remove its end 112 from obstructing the movement of the blade. However, when the new blade is bottomed against the surface 88, the spring is released to permit its end 112 to again engage the notch 110 and secure the new blade in place.

In order to prevent the retaining spring 108 from being accidentally and unnecessarily depressed while the scalpel 10 is being handled, and thereby inadvertantly releasing the blade 16, a slide shim or plate member 114 is inserted between the spring 108 and the surface of the land 92 of the retaining ring 90. The slide member or shim 114 has a hole 116 at its forward end through which the head end 118, of the spring 108, passes into the front hole 100 of the ring 90, while the slide plate 114 engages beneath and is normally held under the overlapping tab 96. The slide plate 114 is permitted to be swung about the axis of spring head end 118 to a broken line position parallel to the surface of the land 92 to one side of the spring 108 as shown by the double arrows D in FIG. 4.

The slide plate 114 is provided with a slit 120 extending transversely to the longitudinal axis of the plate 114, which slit defines a resilient finger 122 at the rear most edge of which is a notch 124 which is adapted to engage with the spring 108 to hold the slide in place beneath the longitudinal tab 96. With the plate 114 secured in this position, the shim 114 takes up the space between the surface 92 and spring 108 so that the spring cannot be depressed or have its end 112 displaced from the notch 110 in the blade 16. Hence, until the plate 114 is disengaged at 124 from the spring 108, it cannot pivot to its broken line position to enable displacement of the end 112 from notch 110 of the blade 16.

It is thus readily apparent from the foregoing description that the earlier enumerated objects have been met and that a scalpel is provided in which the blade 16 has a universal movement in the arc defined by the arrows B, between a position in line with the axis "X" of the handle and 90 degrees offset from or perpendicular to the axis "X" of the handle. The cutting edge of the blade 16 also may be rotated clockwise and counterclockwise (arrow C) about its own axis Y—Y through an arc of at least 360 degrees. This enables the surgeon to position the cutting edge of the blade 16 in any desired position with respect to the surface to be surgically treated without having to remove the blade from its holder and without having to change blades in the holder and without having to change scalpels. The same surgical blade may be used regardless of the angular position in which the cutting surface must be treated.

Locking of the blade 16 in its selected position of operation is further insured by the mechanism described, which also permits the release of the blade enabling it to be moved to any universal selected position of usage. This is done by simple upward movement of the finger ridge 28 at the proximal end of the lever 26. Even a relatively quick upward movement of the lever 26 will enable release of the pressure of the plate 80 against the ball 74 allowing the blade to be easily moved to its desired position and then quickly relocked in its new position of usage.

Another feature of the invention is apparent from the mechanism utilized to retain the blade in the rotating chuck mechanism. Not only does the combination of ring 90 and wire spring 108 permit quick and easy removal of the blade for substitution with another blade, but it permits the use of blades which do not have any special configuration. That is, the blades need only be flat and have a single retaining notch 110 for cooperation with the retaining spring.

The foregoing disclosure sets forth several forms and embodiments. Changes, additional embodiments, and modifications will also be apparent to those skilled in this art. The disclosure, therefore, is to be taken as illustrative and not limiting of the invention.

What is claimed is:

1. A scalpel comprising an elongated cylindrical handle closed at its proximal end and having a hollow sleeve portion formed with a spherical socket and cleft at its distal end adapted to receive a chuck in which a blade is fixedly secured, said chuck including a spherical base slidably seated in said socket for rotation of said chuck in an arc of at least 360 degrees therein and a shank extending through said cleft for swinging said chuck in an arc of at least 90 degrees, means for releasably locking said chuck in a selected position of rotation and swing comprising a stop plate slidable axially within the sleeve portion in opposition to the spherical base of said chuck and an over-the-center crank mechanism aligned with said stop plate in said handle for reciprocally displacing said stop plate within said sleeve to alternately effect proximal movement of said stop plate into an inoperative position free of said spherical base thereby permitting rotation of said chuck and distal movement of said stop plate into an operative position pressed against said spherical base to lock said chuck against rotation, said over-the-center crank mechanism including a lever extending radially outward from said handle when said stop plate is in its inoperative position and lying flat against said handle when said stop plate is in its operative position, said lever being manipulatable conjointly with the manipulation of said handle by a single hand of the user.

2. The scalpel according to claim 1, wherein said crank mechanism comprises a crank head mounted within said handle midway between the proximal and distal ends thereof to revolve in an eccentric path about an axis transverse to the central axis of said handle, a first rod interposed between said stop plate and said crank head and a second rod interposed between said crank head and said proximal end of said handle, said second rod engaging said crank head so that when said crank head is revolved in one direction said second rod resiliently biases said head and first rod proximally to move said stop plate into the inoperative position and when said crank head is revolved in the other direction and crank head and first rod are resiliently biased distally to move said stop plate into the operative position, and wherein said lever is attached to said crank head.

3. A scalpel comprising an elongated cylindrical handle closed at its proximal end and having a hollow sleeve portion formed with a spherical socket and cleft at its distal end adapted to receive a chuck in which a blade is fixedly secured, said chuck including a spherical base sidably seated in said socket for rotation of said chuck in an arc of at least 360 degrees therein and a shank extending through said cleft for swinging said chuck in an arc of at least 90 degrees, means for releasably locking said chuck in a selected position of rotation and swing comprising a stop plate slidable axially within the sleeve portion in opposition to the spherical base of said chuck and an over-the-center crank mechanism to alternately effect proximal movement of said stop plate into an inoperative position free of said spherical base thereby permitting rotation of said chuck or distal movement of said stop plate into an operative position pressed against said spherical base to lock said chuck against rotation, said crank mechanism comprising a crank head mounted within said handle midway between the proximal and distal ends thereof to revolve in an eccentric path about an axis transverse to the central axis of said handle, a first rod interposed between said stop plate and said crank head and a second rod interposed between said crank head and said proximal end of said handle, said second rod engaging said crank head so that when said crank head is revolved in one direction said second rod resiliently biased said head and first rod proximally to move said stop plate into the inoperative position and when said crank head is revolved in the other direction said crank head and first rod are resiliently biased distally to move said stop plate into the operative position, and a lever intergrally connected to said crank lever and extending radially outward from said handle when said crank head is in its inoperative position and lying flat against said handle when said crank head is in its operative position.

4. The scalpel according to claim 3, wherein said chuck shank is provided with an axial slot in which said blade is received, a collar surrounding said chuck shank to encompass said blade, and means for releasably securing said collar and the blade to said chuck shank.

5. The scalpel according to claim 4, wherein said means for securing said collar and said blade comprises a wire spring passing through said collar, the chuck shank and at least part of said blade, said spring being releasable from the blade to permit removal of the blade from said slot without disengagement from said collar and chuck shank.

6. The scalpel according to claim 4, wherein said sleeve portion comprises a separable hollow tubular member threadedly connected at its distal end to said handle, said sleeve being thereby capable of adjusting the distance of said socket to said crank head and the pressure of said first rod on said stop plate.

7. The scalpel according to claim 3, wherein said crank head and lever are planar and said handle is provided with a diametric slot into which said crank head is located.

8. The scalpel according to claim 7, wherein said crank head is provided with a notch at its distaledge to receive said first rod and a notch on its proximal edge to receive said second rod, said notches being offset from the center of revolution of said crank head.

9. The scalpel according to claim 7, including a pintle extending transverse to said slot and wherein said crank head has a central substantial elliptical hole extending substantially in the transverse direction of said slot and surrounding said pintle.

* * * * *